(12) United States Patent
Estocado

(10) Patent No.: US 8,276,287 B2
(45) Date of Patent: Oct. 2, 2012

(54) SKIN AND WOUND ASSESSMENT TOOL

(75) Inventor: Nancy Ann Estocado, Las Vegas, NV (US)

(73) Assignee: N.E. Solutionz, LLC, Las Vegas, NV (US)

( * ) Notice: Subject to any disclaimer, the term of this patent is extended or adjusted under 35 U.S.C. 154(b) by 412 days.

(21) Appl. No.: 12/606,773

(22) Filed: Oct. 27, 2009

(65) Prior Publication Data

US 2011/0098539 A1    Apr. 28, 2011

(51) Int. Cl.
*G01B 1/00* (2006.01)
*A61B 5/00* (2006.01)

(52) U.S. Cl. .................. 33/511; 33/1 BB; 33/679.1

(58) Field of Classification Search ............ 33/511, 33/512, 679.1
See application file for complete search history.

(56) References Cited

U.S. PATENT DOCUMENTS

| | | | | |
|---|---|---|---|---|
| 898,565 | A * | 9/1908 | Duncan | 33/679.1 |
| 999,425 | A * | 8/1911 | Zaino | 33/11 |
| 1,121,289 | A * | 12/1914 | Robertson | 33/679.1 |
| 1,663,895 | A * | 3/1928 | Wolfe et al. | 33/11 |
| 1,763,091 | A * | 6/1930 | Cangemi | 33/11 |
| 1,776,393 | A * | 9/1930 | Onorato | 33/11 |
| 1,904,234 | A * | 4/1933 | Hoskin et al. | 378/163 |
| 2,503,398 | A * | 4/1950 | Lindsey | 235/70 R |
| 2,720,707 | A * | 10/1955 | Bickley | 33/833 |
| 2,928,182 | A * | 3/1960 | Malczewski | 33/679.1 |
| 3,245,882 | A * | 4/1966 | Guthrie | 435/29 |
| 3,559,881 | A * | 2/1971 | Maison | 235/61 B |
| 3,819,490 | A * | 6/1974 | Klingstrom et al. | 435/287.7 |
| 4,389,782 | A | 6/1983 | Webster | |
| 4,420,891 | A * | 12/1983 | Orem | 33/476 |
| 4,483,075 | A | 11/1984 | Kundin | |
| 4,517,747 | A * | 5/1985 | Morin | 33/512 |
| 4,969,271 | A * | 11/1990 | Sump | 33/431 |
| 5,014,438 | A * | 5/1991 | Gravel | 33/494 |
| 5,018,531 | A * | 5/1991 | Hartman | 33/483 |
| 5,163,228 | A * | 11/1992 | Edwards et al. | 33/1 N |
| 5,167,076 | A * | 12/1992 | Sump | 33/431 |
| 5,170,570 | A * | 12/1992 | Mays, Jr. | 33/512 |
| 5,265,605 | A | 11/1993 | Afflerbach | |
| 5,534,952 | A * | 7/1996 | Zanecchia et al. | 33/555.1 |
| 5,605,165 | A | 2/1997 | Sessions et al. | |

(Continued)

FOREIGN PATENT DOCUMENTS

DE     3622073     1/1988

(Continued)

OTHER PUBLICATIONS

Aranz Medical Ltd., Silhouette Mobile Product Sheet, 2006.

(Continued)

*Primary Examiner* — Yaritza Guadalupe-McAll
(74) *Attorney, Agent, or Firm* — Cuenot, Forsythe & Kim, LLC

(57) ABSTRACT

An L-shaped diagnostic tool is preferably made from paper with a backing having a contact adhesive. Each arm has a ruler, with origins co-aligned at the internal corner of the intersection of the arms. One arm has representative color images of afflictions for each of the various ranks within a classification system. The other arm contains textual descriptions of the salient features of afflictions in each rank. A photograph of the L-shaped tool placed around the affliction may be taken for diagnostic and monitoring purposes.

7 Claims, 10 Drawing Sheets

U.S. PATENT DOCUMENTS

| | | | | |
|---|---|---|---|---|
| 5,678,317 A * | 10/1997 | Stefanakos | | 33/512 |
| 5,741,212 A * | 4/1998 | Matthews | | 33/512 |
| 5,969,822 A | 10/1999 | Fright et al. | | |
| 6,026,579 A * | 2/2000 | Autrey | | 33/431 |
| 6,159,167 A | 12/2000 | Hardin-Naser | | |
| 6,351,893 B1 * | 3/2002 | St. Pierre | | 33/563 |
| 6,408,529 B1 * | 6/2002 | Hodges | | 33/429 |
| 6,540,756 B1 * | 4/2003 | Vaughan | | 33/18.1 |
| 6,725,559 B2 * | 4/2004 | Burt, Jr. | | 33/653 |
| 6,993,851 B2 * | 2/2006 | Cohen | | 33/512 |
| 7,376,456 B2 | 5/2008 | Marshik-Geurts et al. | | |
| 7,401,413 B1 * | 7/2008 | Nelson | | 33/512 |
| 7,412,780 B2 * | 8/2008 | Holder | | 33/562 |
| 7,421,789 B1 * | 9/2008 | Sullivan | | 33/3 R |
| 7,614,155 B2 * | 11/2009 | Healey | | 33/195 |
| 7,975,395 B2 * | 7/2011 | Keller et al. | | 33/451 |
| 2003/0213140 A1 * | 11/2003 | Burt, Jr. | | 33/653 |
| 2004/0107592 A1 * | 6/2004 | Matlis | | 33/512 |
| 2004/0134084 A1 * | 7/2004 | Vanneste | | 33/512 |
| 2006/0005409 A1 * | 1/2006 | Cohen | | 33/512 |
| 2006/0032068 A1 * | 2/2006 | Sherman et al. | | 33/566 |
| 2006/0075647 A1 * | 4/2006 | Garrick | | 33/511 |
| 2007/0157483 A1 * | 7/2007 | DuMais | | 33/512 |
| 2007/0240321 A1 * | 10/2007 | Shapiro | | 33/471 |
| 2008/0234552 A1 * | 9/2008 | Averbach | | 600/300 |
| 2008/0289199 A1 * | 11/2008 | Healey | | 33/195 |
| 2009/0013546 A1 * | 1/2009 | Keller et al. | | 33/451 |
| 2009/0119939 A1 * | 5/2009 | Rosso et al. | | 33/479 |
| 2009/0126210 A1 * | 5/2009 | Ball et al. | | 33/3 B |
| 2009/0213213 A1 | 8/2009 | Fright et al. | | |
| 2011/0098539 A1 * | 4/2011 | Estocado | | 33/1 BB |

FOREIGN PATENT DOCUMENTS

| | | |
|---|---|---|
| JP | 2003000568 A | 1/2003 |
| WO | 2005002438 A1 | 1/2005 |

OTHER PUBLICATIONS

Bosio et al., A Proposal for Classifying Peristomal Skin Disorders: Results of a Multicenter Observational Study, Ostomy Wound Manage., 53(9):38-43, Sep. 1, 2007.

Patent Cooperation Treaty, "PCT Search Report and Written Opinion of the International Searching Authority," for International Application PCT/US2010/053559, Jun. 3, 2011, 8 pages.

* cited by examiner

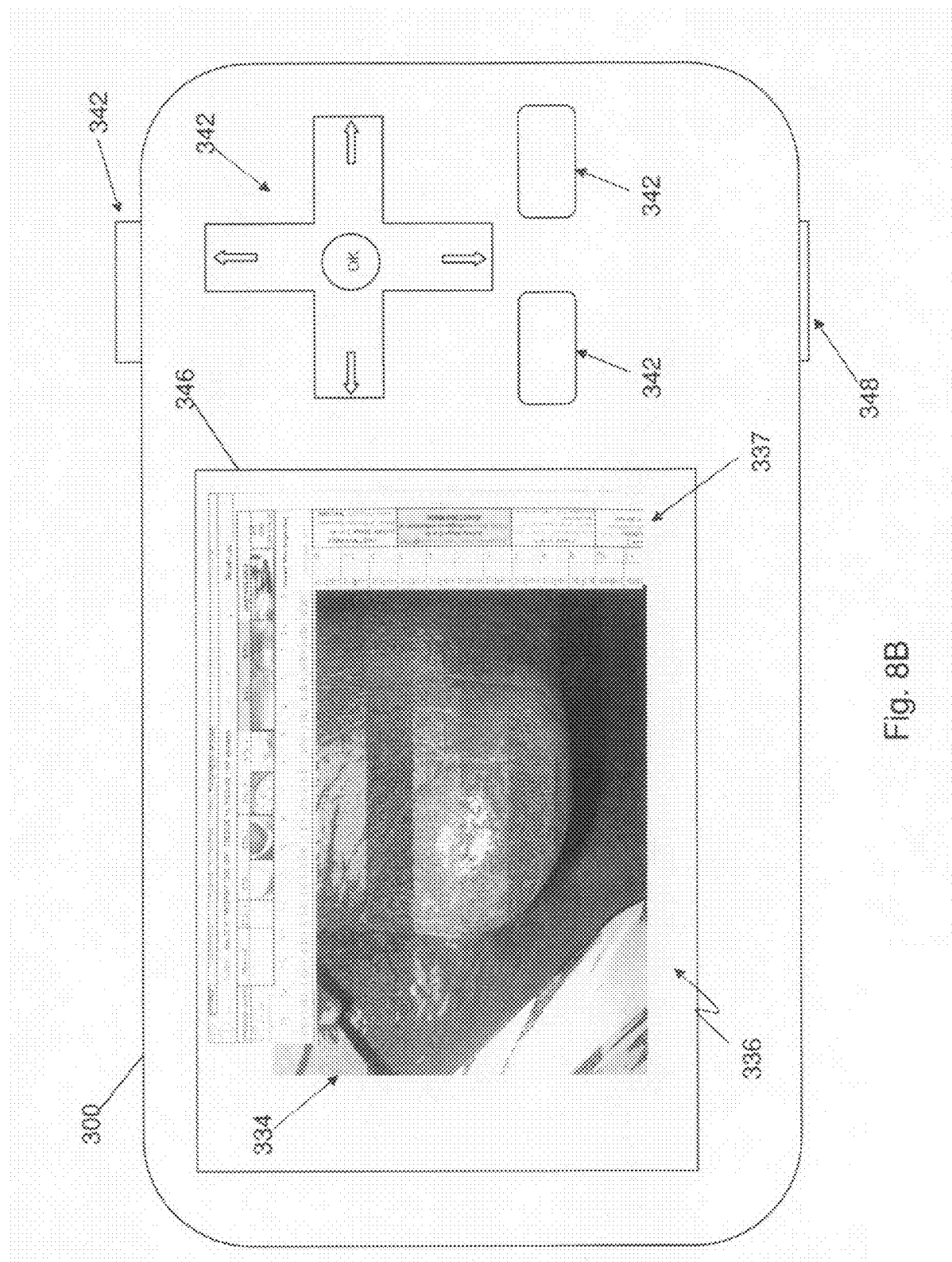

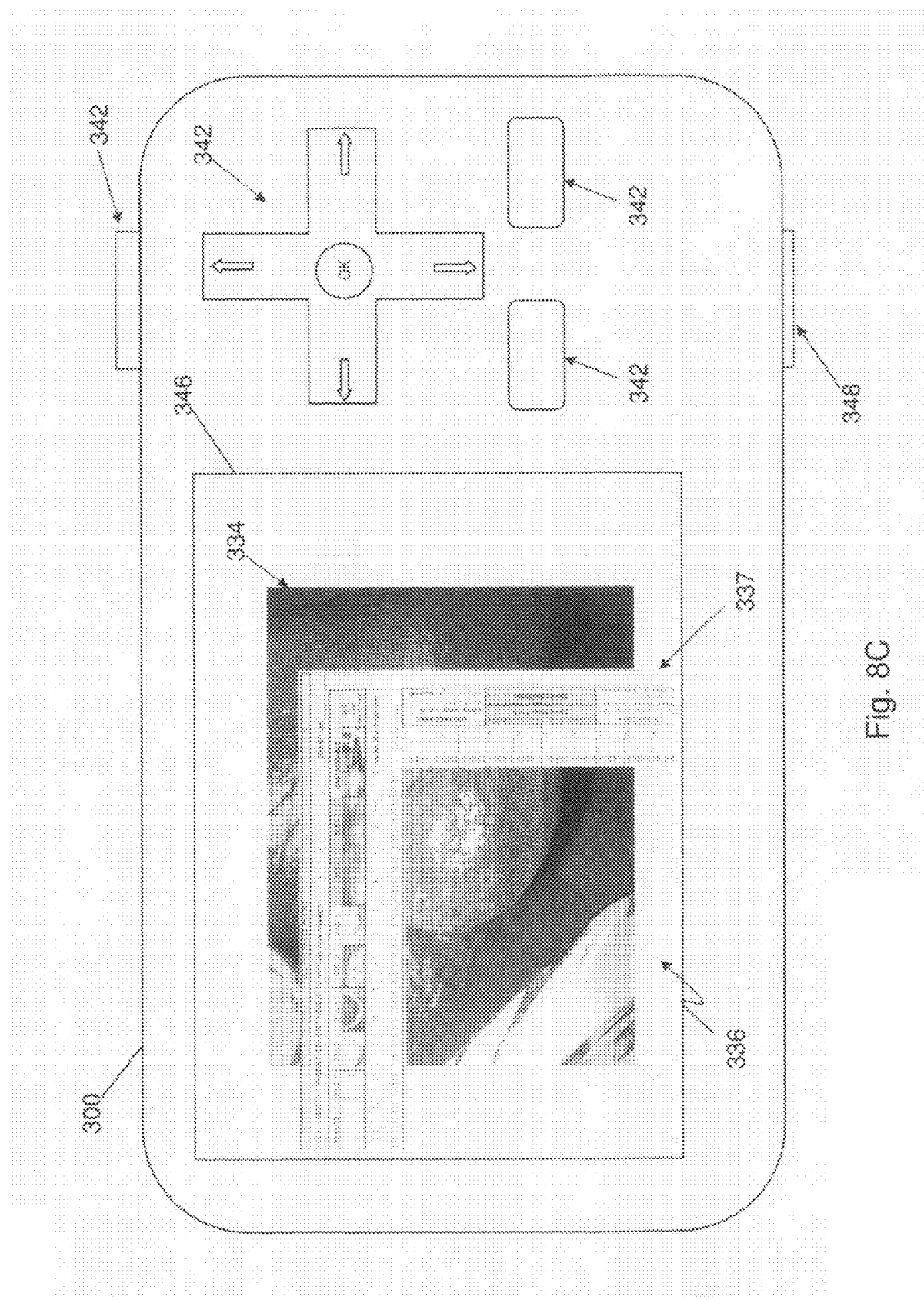

SKIN AND WOUND ASSESSMENT TOOL

COPYRIGHT AUTHORIZATION

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

FIELD OF THE INVENTION

The present invention relates generally to assessment tools. More particularly, various embodiments disclose an L-shaped measuring tool that facilitates easy and consistent categorizations of patient wounds.

BACKGROUND OF THE INVENTION

The accurate and consistent diagnosis of patient health parameters is essential for the proper staging and treatment of the patient. Consistency in measurement results over time for a single patient is vital to ensure that the actual progress or degradation of the health of the patient is being properly determined. Consistency in measurement results across patients is also vital to ensure that treatment protocols and their underlying data are applied consistently from patient to patient.

Many types of patient health criteria may be classified along a sliding scale depending upon the severity of the affliction. For example, burns have a classification scale of severity ranging from first degree (least severe) up to third degree (most severe). Other classification scales exist for other types of afflictions, such as the Wagner's Scale for foot ulcers, the Payne Martin Classification for skin tears, and the National Pressure Ulcer Advisory Panel (NPUAP) Pressure Ulcer Staging System. Each of these classification scales has a known and accepted classification system that permits a practitioner to assess an affliction against certain predefined standards and assign to the affliction a classification value corresponding to one of a plurality of ranks along the severity scale. Changes of this value in time thus correspond to improving or deteriorating conditions of the affliction and permit the rapid assessment of patient health and progress. It is therefore critical for staging and treatment purposes that clinicians be able to accurately and consistently assess an affliction and classify it into its proper rank along a known scale for that affliction.

Accordingly, there is an immediate need for assessment measuring tools that permit a practitioner to accurately and consistently classify an affliction.

SUMMARY OF THE INVENTION

In one aspect an L-shaped diagnostic tool is disclosed. The diagnostic tool comprises a first arm and a second arm joined in an L-shaped configuration. A top surface of the first arm includes a graphical ranking guide, which has a plurality of images that graphically illustrate salient rank classifier indicia for a classification system. Each of the images corresponds to at least one of the ranks within the classification system. In preferred embodiments, each of the ranks has at least one corresponding image, and the images are color images.

In certain preferred embodiments the top surface of the second arm includes a descriptive ranking guide, which has a plurality of rank descriptors that contain text describing salient rank classifier indicia for each of the ranks.

In particularly preferred embodiments the L-shaped tool is provided by a paper substrate, and the bottom surface of the paper substrate comprises a pressure-sensitive adhesive.

Preferred embodiments of the diagnostic tool also include a first ruler and a second ruler respectively disposed on the first arm and the second arm, the origins of which are co-aligned at the internal corner of the L-shaped device.

In certain embodiments the top surface of the first arm or the second arm may further comprise one or more fields configured for the notational entry of subject and/or assessment information.

In another aspect a diagnostic method is disclosed. A practitioner obtains an embodiment L-shaped diagnostic tool and places the tool adjacent to an affliction so that the arms extend around the affliction but preferably do not touch the affliction. The practitioner then takes a picture that is framed to include the affliction and at least a portion of the L-shaped diagnostic tool. The graphical ranking guide, the descriptive ranking guide or both are used to determine a rank of the affliction within the classification system.

In certain embodiments a print of the picture is made and the print is attached to a form or chart of the subject suffering from the affliction.

In yet other embodiments the first ruler, the second ruler or both are used to estimate one or more of the area of the affliction, extent of the affliction along the first arm, and extent of the affliction along the second arm.

BRIEF DESCRIPTION OF THE DRAWINGS

FIGS. 8A-8C show back views of the camera of FIG. 7 with image manipulation being performed by a user according to an embodiment assessment method.

DETAILED DESCRIPTION

For purposes of the following, a "subject" is any person, animal, plant, system or the like upon which measurements may be made.

An "affliction" broadly includes a wound, skin abnormality, blemish, disease, state or condition exhibited by a subject that may exhibit one or more measurable symptoms or characteristics.

A "clinician" or "practitioner" is a person that takes measurements of a subject, and may include a doctor, nurse, physical therapist, laboratory personnel or the like.

A "value" includes a number, letter, symbol, word or the like.

A "classification system" is an assessment procedure that permits a clinician to assign a value to an affliction based upon one or more measurable symptoms or characteristics. Each value corresponds to one of a plurality of ranks, each rank being associated with a predefined state or condition of the affliction. Ranks, and their corresponding values, are typically ordered by severity or the like. By way of example, classification systems include the burn classification system, the Wagner's Scale for foot ulcers, the Payne Martin Classification for skin tears, the NPUAP pressure ulcer staging system, the Center for Disease Control (CDC) Surgical Wound Classifications, Bruise Classification, Primary Lesions and Secondary Lesions.

"Rank classifier indicia" include one or more symptoms or characteristics of an affliction when in a state or condition corresponding to a rank. Rank classifier indicia may be indicated graphically through illustrations, photographs and the like, as well as textually.

Specific reference is made in the following to the medical fields, for which particularly preferred embodiment devices are adapted, but it should be understood that other embodiment devices may be more widely employed and may not be limited to only the field of medical assessment.

Figure 1:
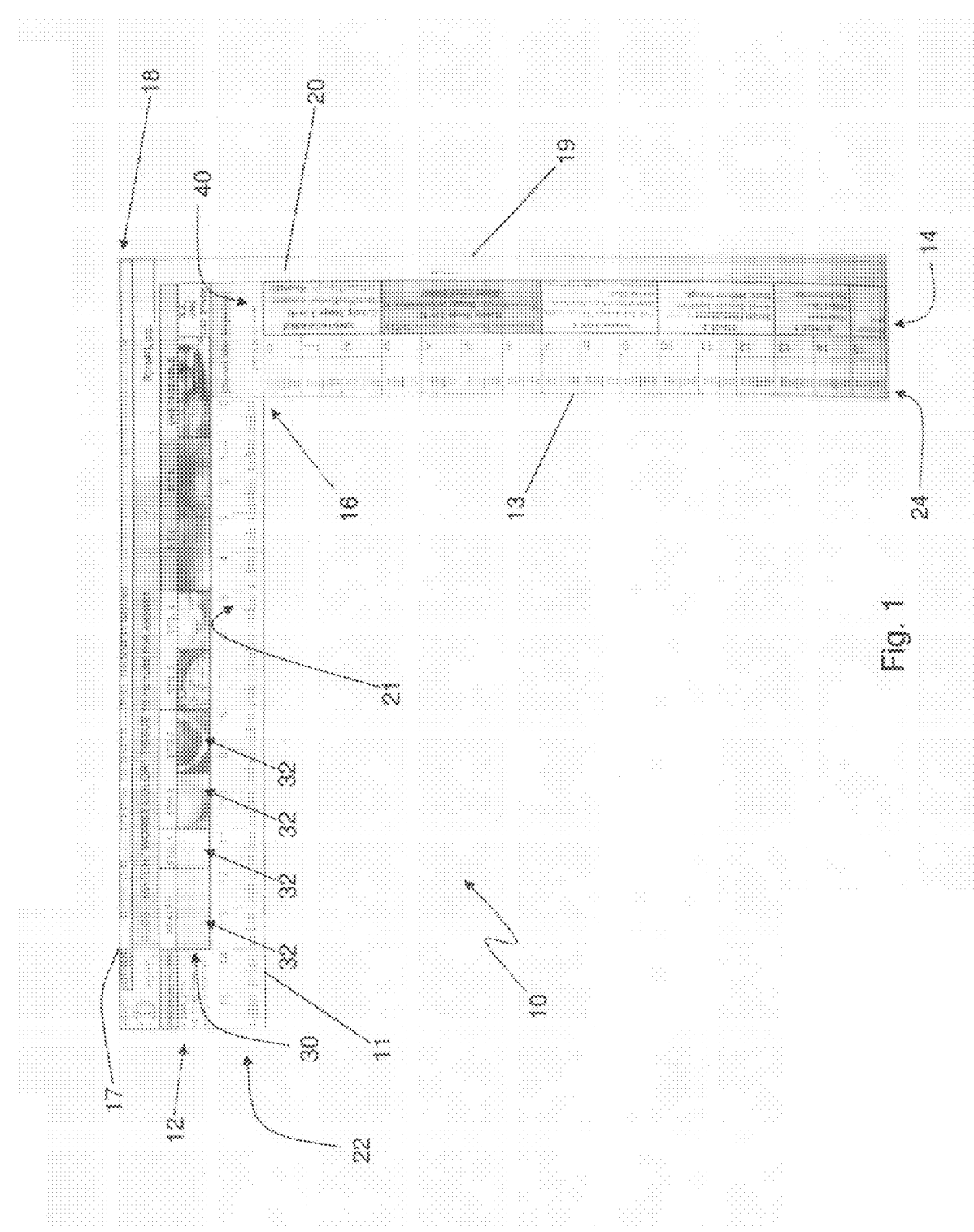
FIG. 1 is a top view of an embodiment diagnostic device.

As known in the field of assessments and diagnostics, and in the medical fields in particular, afflictions of a specific type may be encountered in wide degrees of various states of intensity or severity. Predefined classification systems exist that permit a clinician or practitioner to "pigeon hole" a patient's affliction into a rank based upon severity and thereby record a corresponding value into the patient's chart. Each rank in the classification system is typically characterized by corresponding rank classifier indicia that clinicians or practitioners are familiar with and against which clinicians or practitioners compare the affliction to determine the corresponding rank. An embodiment assessment classification device 10 is shown in FIG. 1, which permits rapid, accurate and repeatable rank determinations by clinicians or other users of the device 10.

By way of specific example, the diagnostic classification device 10 is configured to permit the classification skin tissue wounds. It will be appreciated that devices configured to permit the classification of other types of afflictions are possible. Skin pressure ulcer wounds are typically classified into six or more ranks. These ranks may be ordered by the severity of the skin tissue wound and include, in order, healed, stages one to four, suspected deep tissue injury (DTI), and unstageable. "Healed" is the degenerate case in which there is no tissue wound or normal skin, and the corresponding rank classifier indicia would be those characteristics of normal skin.

Rank classifier indicia for stage I wounds include intact skin with localized, non-blanchable redness that is typically over a bony prominence. It is noted that with respect to darkly pigmented skin, the corresponding stage I rank classifier indicia may not include visible blanching, although the color of the wound may differ from the surrounding area. Additional stage I rank classifier indicia pain in the area, or the are being softer, warmer or cooler than the surrounding tissue.

Corresponding rank classifier indicia for stage II wounds include a partial loss of thickness of the dermis, which presents as a shallow open ulcer having a smooth reddish or pinkish wound bed, but the wound itself presents without slough. Stage II rank classifier indicia may also include an open or ruptured, serum-filled blister. Additional stage II rank classifier indicia include a shiny or dry, shallow ulcer without slough or bruising.

Stage III rank classifier indicia may include full thickness tissue loss, including visible subcutaneous fat, and/or moist, red, bubbly granulation tissue, but not including exposed visible bone, tendon or muscle. Sloughing may be part of stage III rank classifier indicia so long as it does not obscure the depth of tissue loss. Undermining and tunneling are also suitable rank classifier indicia. It will be appreciated that rank classifier indicia may vary depending upon the location of the affliction upon the subject. For example, the depth of a stage III pressure ulcer may vary by anatomical location, and thus corresponding rank classifier indicia may include anatomical position in the context of other symptoms or characteristics.

Stage IV rank classifier indicia include full thickness tissue loss with exposed bone, tendon or muscle. Other rank classifier indicia include slough or eschar in some regions of the wound bed. Undermining and tunneling may also be suitable stage IV rank classifier indicia.

DTI rank classifier indicia include intact skin with purple, maroon or the like coloration, or a blood-filled blister arising from damaged underlying soft tissue arising from pressure, shear or both. Additional rank classifier indicia include pain, or tissue that is firmer, cooler, or warmer, than the adjacent tissue, or that is mushy or boggy. Suitable rank classifier indicia may not be pronounced or obvious in subjects with dark skin tones. Additional rank classifier indicia may include the evolution of the wound, and in particular a thin blister over a dark wound bed that evolves to become covered by thin eschar.

Rank classifier indicia for the unstageable rank include full thickness tissue loss in which the base of the ulcer is covered by slough (which may be yellow, tan, gray, green or brown) and/or eschar (which may be tan, brown or black) in the wound bed. This ranking may be used as a placeholder until enough slough and/or eschar is removed to expose the base of the wound, after which the true depth, and therefore proper stage as characterized above, of the wound may be determined.

Referring again to FIG. 1 in the context of the above-described rank classifier indicia, the device 10 is L-shaped, having a first arm 12 and a second arm 14 that preferably meet at a right angle. An internal origin 16 and an external origin 18 are thereby respectively created by the meeting of the first arm 12 and second arm 14. More specifically, the internal origin 16 is formed by the intersection of the respective internal edges 11 and 13 of the first arm 12 and the second arm 14. Similarly, the external origin 18 is formed at the intersection of the respective external edges 17 and 19 of the first arm 12 and the second arm 14. The L-shaped device 10 is formed from a substrate 20 having a top surface 21 and a bottom surface. The top surface 21 is shown in FIG. 1. The substrate is preferably made from a clean, disposable, single patient use material. More preferably, the substrate 20 is made from paper. In certain preferred embodiments the device 10 meets the requirements for using "clean technique" versus "sterile technique" procedures due to the fact that most wounds are contaminated and thus do not require the more stringent sterile technique protocols. However, other embodiment devices 10 may conform to such "sterile technique" protocols to accommodate, for example, new incision-type wounds made in an operating room, or to accommodate devices 10 placed within a sterile packaging kit, as may be done, for example, with negative wound therapy dressing kits. Devices 10 may therefore be manufactured in accordance with sterile technique methods in a certified sterilization facility and may thus be used, packaged and labeled per national standards. However, other or additional substrate 20 materials are possible, such as coating the top surface, bottom surface or both of the device 10 with antimicrobial or antiseptic agents, such as Silver AG+, Hydroferra Blue, Chlorhexidine Gluconate, Dakins, Acetic Acid, Betadine, Aluminum Salts and the like.

The device 10 may also be laminated with an approved-see through covering that may be disinfected between patient use.

Figure 2:
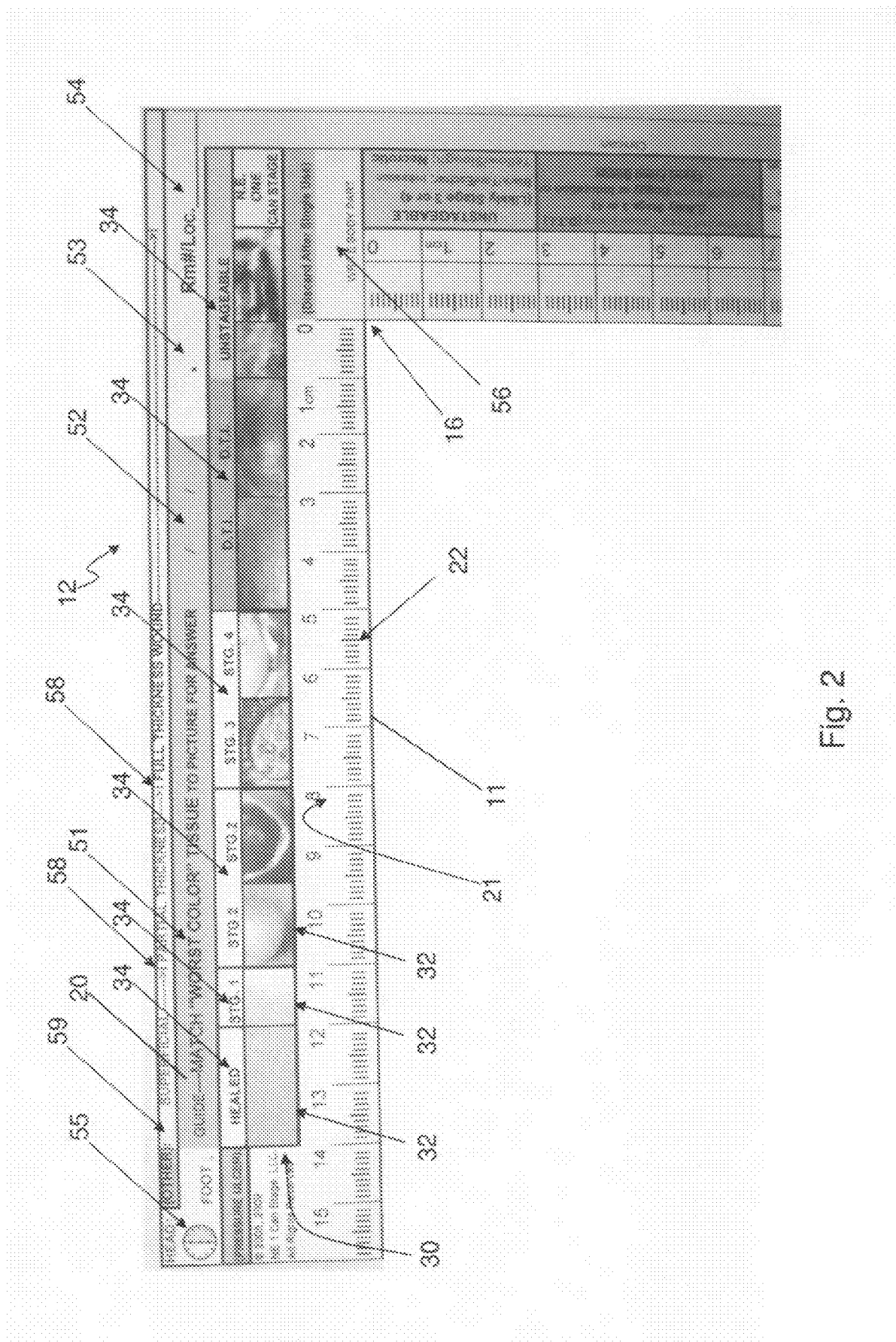
FIG. 2 is a detailed view of a first arm of the device shown in FIG. 1.

A detailed view of the top surface 21 of the first arm 12 is shown in FIG. 2. The top surface 21 of the first arm 12 may include a first ruler 22, which is preferably immediately adjacent to, and runs along, the internal side 11. The first ruler 22 may be formed by any suitable means, but is preferably formed by ink markings. The origin (or zero-point) of the first ruler 22 may be advantageously aligned with the internal origin 16.

The top surface 21 of the first arm 12 also includes a graphical ranking guide 30. The graphical ranking guide 30 includes a plurality of graphical images 32, which are preferably color photographs or color illustrations, although it will be appreciated that any suitably clear, representative images as discussed in the following may be utilized. Color images are highly preferred, however, as they uniquely and intuitively provide color information that may be highly relevant to rank classifier indicia. Color graphical images 32 provide the unappreciated benefit of more consistent and reproducible affliction rank classifications by practitioners, which is highly desirable for patient health and treatment purposes. Each graphical image 32 corresponds to a rank in the classification system for the affliction to be diagnosed with the aid of device 10. Each rank in the classification system is preferably provided at least one corresponding graphical image 32, and as shown in FIGS. 1 and 2 may in some cases include two or more representative images 32. Each graphical image 32 graphically presents to the practitioner rank classifier indicia that is representative for that rank corresponding to the image 32. Adjacent to each graphical image 32, or groups of graphical images 32, may be a corresponding rank title indicator 34, which indicates the name of that rank for the corresponding graphical image(s) 32. By way of example, below rank title indicator 34 "Healed" is a graphical image 32 of normal skin, which corresponds to the "Healed" rank for the wound classification system employed by the device 10. Similarly, two graphical images 32 are shown, each corresponding to a stage two wound, above each of which is provided the rank title indicator 34 "STG. 2", indicating the rank of stage two. In the same vein, graphical images 32 are provided for stages one, three and four, as well as DTI and unstageable wounds, for each of which is further included a corresponding rank title indicator 34.

Figure 3:
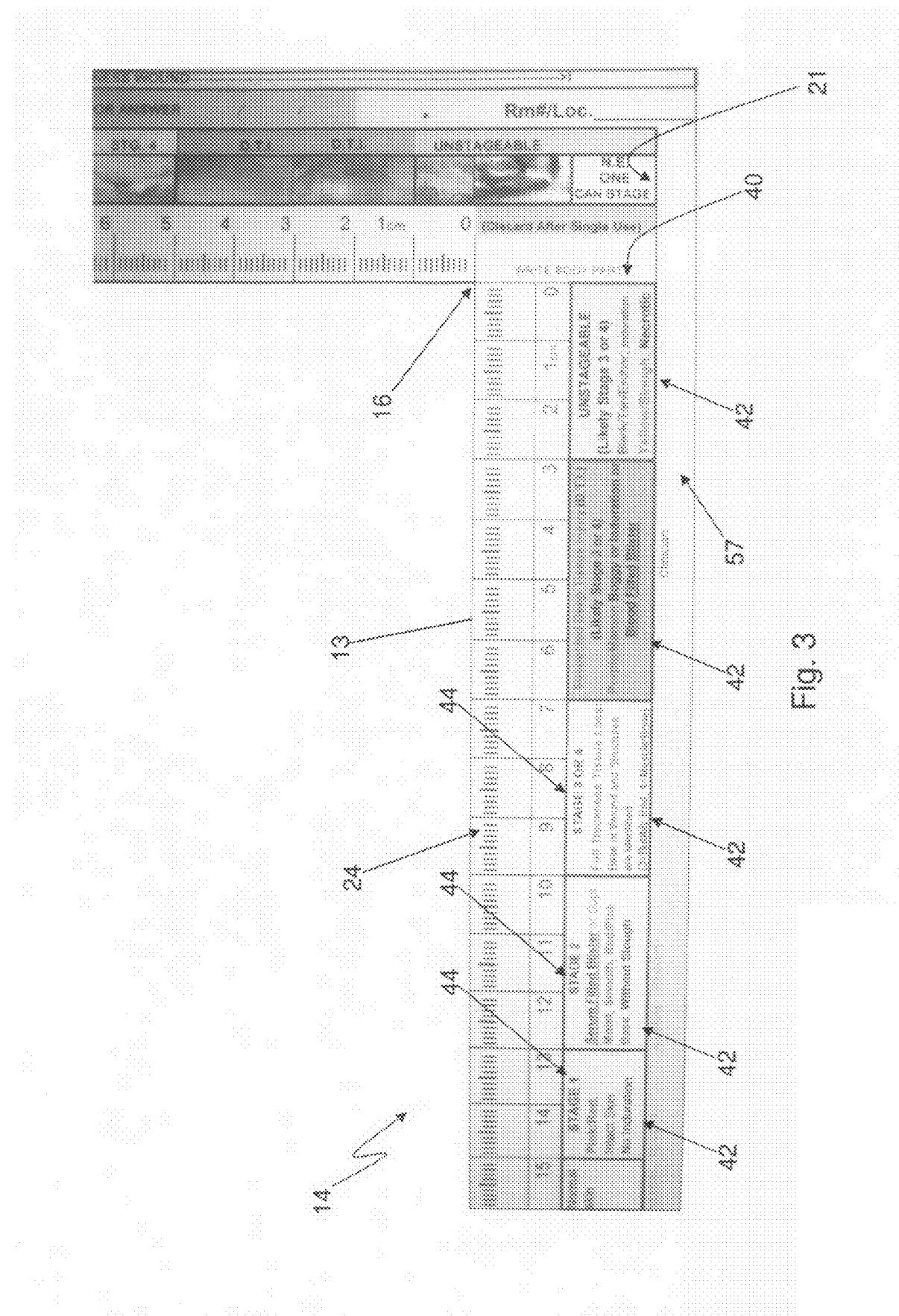
FIG. 3 is a detailed view of a second arm of the device shown in FIG. 1.

A detailed view of the top surface 21 of the second arm 14 is shown in FIG. 3. The top surface 21 of the second arm 14 may include a second ruler 24, which is preferably immediately adjacent to, and runs along, the internal side 13 of the second arm 14. The second ruler 24 may be formed in the same manner as the first ruler 22. The origin (or zero-point) of the second ruler 24 may be advantageously aligned with the internal origin 16. The first ruler 22 and the second ruler 24 thus provide a convenient Cartesian coordinate system that may be used to measure, for example, the area of an affliction, the extent of the affliction along the first arm 12, and the extent of the affliction along the second arm 14.

The top surface 21 of the second arm 14 also includes a descriptive ranking guide 40. The descriptive ranking guide 40 includes a plurality of rank descriptors 42 that contain text describing the salient features of the respective rank classifier indicia for that rank. Each rank descriptor 42 corresponds to a rank in the classification system for the affliction to be diagnosed with the aid of device 10. Each rank in the classification system is preferably provided at least one corresponding rank descriptor 42, but in some cases two or more ranks may share portions of a common rank descriptor 42, as shown in FIGS. 1 and 3. Each rank descriptor 42 has text that describes to the practitioner the most significant rank classifier indicia that is representative for that rank or group of ranks corresponding to the descriptor 42. Adjacent to, or with, each rank descriptor 42 may be a corresponding rank title indicator 44, which indicates the name of that rank, or group of ranks, for the corresponding rank descriptor 42. By way of example, below rank title indicator 44 "Stage 3 or 4" is text describing the most salient features common to Stage 3 ranked and Stage 4 ranked afflictions in the wound classification system; also included are descriptors that are respectively specific to Stage 3 ranked afflictions and Stage 4 ranked afflictions. In contrast, Stage 1 and Stage 2 ranks each have their own rank descriptor 42 and corresponding rank title indicators 44.

As shown in FIGS. 2 and 3 the device 10, and preferably the top surface 21 of the device 10, may include additional information, and in particular may include lines, boxes or forms that may be filled in by the practitioner. For example, the device 10 may include brief instructions for use 51, a date field 52, a subject initial field 53, a subject location field 54, an anatomical position (the device 10 is preferably positioned at 12 O'clock on the subject to standardize the method) field 55, an affliction location (body part) field 56 (i.e., where the affliction is located on the subject), a field for the name of the practitioner 57 and so forth.

It will be appreciated that the embodiment device 10 is not limited to merely one categorization system. It is possible, for example, to provide the first arm 12 with a graphical ranking guide and corresponding descriptive ranking guide for a first classification system, and provide the second arm 14 with a graphical ranking guide and corresponding descriptive ranking guide for a second classification system. Variations on this theme are also possible. By way of specific example, the embodiment device 10 includes the graphical ranking guide 30 and corresponding descriptive ranking guide 40 for the NPUAP Pressure Ulcer Staging System. However, first arm 12 further includes an abbreviated descriptive ranking guide 59 for "Other" skin problems. The abbreviated ranking guide 59 may simply include, for example, rank title indicators and appropriate spacers 58, as discussed below. Generally speaking, all skin wounds may be divided into either pressure wounds, which may then be categorized as indicated above, or "Other" types of wounds, which have their own categorization system. The "Other" categorization system has three ranks for wounds, which may be labeled superficial, partial thickness and full thickness. Rank classifier indicia for the "superficial" rank include intact skin with redness of a localized area or damage to the epidermis layer of skin. Rank classifier indicia for "partial thickness" include damage to the epidermis and dermis layers of the skin; such damage may be superficial and presents as a red, smooth, shallow crater, abrasion or serum-filled blister. Rank classifier indicia for "full thickness" include damage through the skin to the subcutaneous layer of skin and even to the structures of muscle tendon or bone; it may present as a deep crater and may even tunnel into surrounding subcutaneous tissue.

As shown in FIG. 2, the abbreviated descriptive ranking guide 59 of the second classification system may be positioned and designed so as to align with the graphical ranking guide 30 of the first classification system; in this manner rank classifier indicia common to both systems may be beneficially employed on the device 10. For example, as shown in the device 10, one or more images 32 from one or more ranks in a finely-grained first classification system may be shared to illustrate a single rank in a coarsely-grained second classification system 59. The appropriate grouping of images 32 for each rank in the coarsely-grained second classification system 59 may be indicated by spacers 58 or the like, such as arrows or any other suitable grouping indicator.

Figure 4:
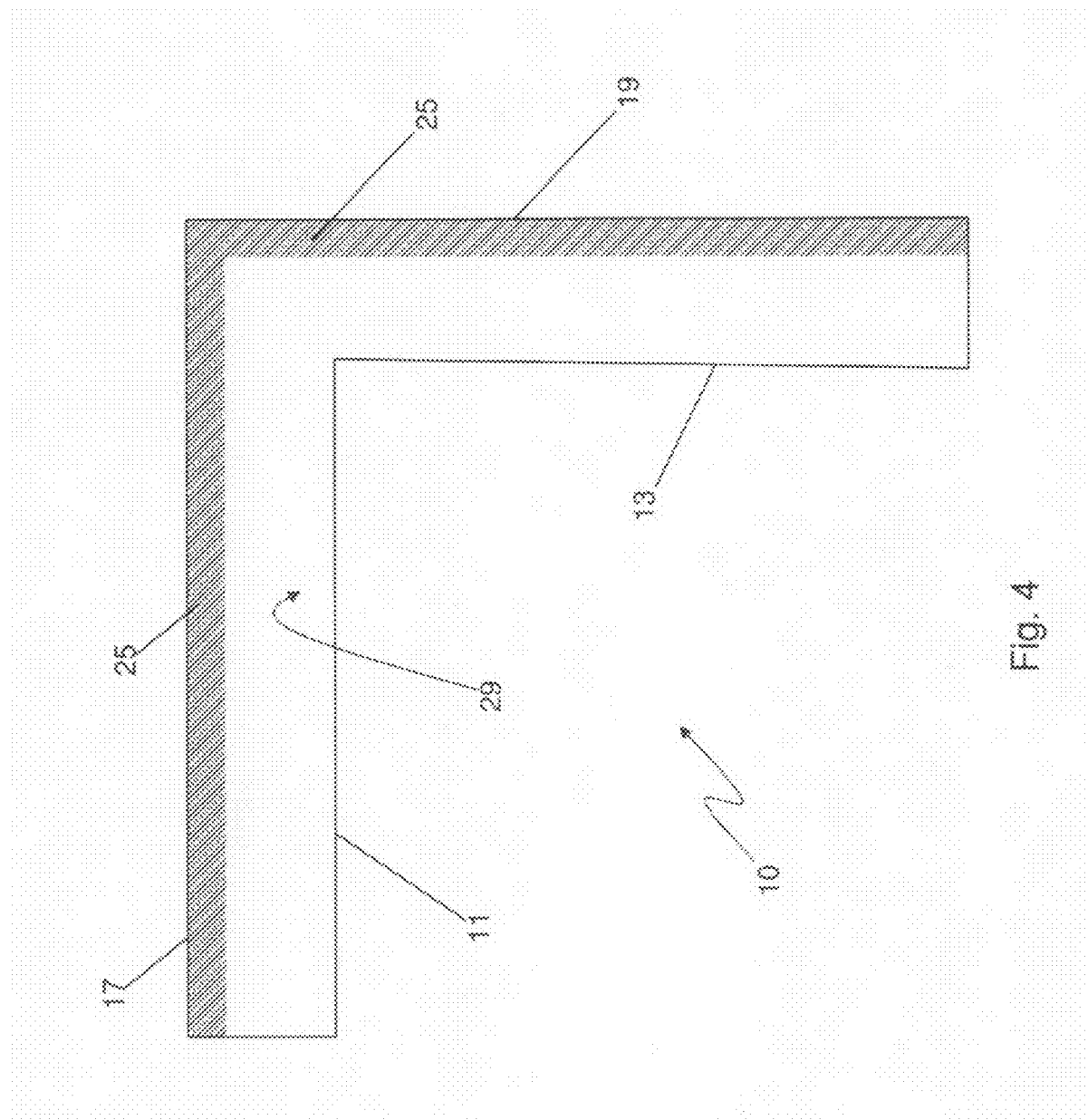
FIG. 4 is a bottom schematic view of the device shown in FIG. 1.

FIG. 4 shows the bottom surface 29 of the embodiment device 10. As illustrated in FIG. 4, the bottom surface 29 of the substrate 20 preferably includes a low-tack, pressure sensitive adhesive 25, such as is used on sticky notes, EKG electrodes, transdermal drug patches and the like. Other tacky surfaces may be used, such as silicone, or no tacky surfaces may be used if there is a know allergy to adhesive or silicone products. Any suitable adhesive may be used as known in the art. The device 10 preferably meets guidelines and is labeled as a "latex free" product. In preferred embodiments the adhesive 25 is a strip approximately 20 cm long and 4 cm wide that runs immediately adjacent to the external edges 17, 19 of the substrate 20. It will be appreciated, however, that other placements and locations of the adhesive 25 are possible. For example, the adhesive 25 could be positioned to run adjacent to the internal edges 11, 13 of the substrate 20. Or, the adhesive 25 may cover the entire bottom surface 29.

Figure 5:
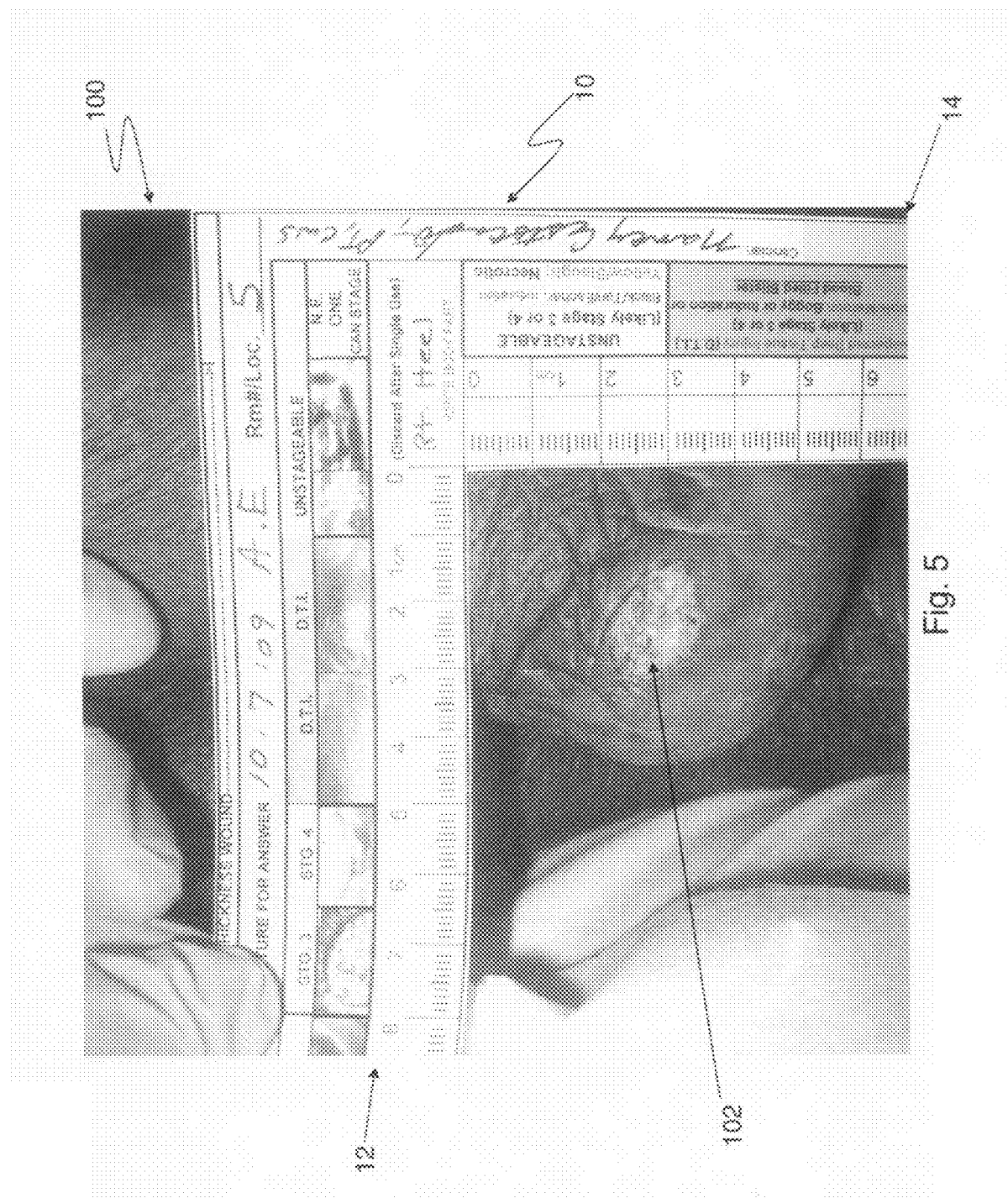
FIG. 5 illustrates use of an embodiment device with a subject.

FIG. 5 illustrates how the embodiment device 10 may be used with a subject 100. With further reference to FIG. 5, the device 10 may be positioned so that the arms 12, 14 extend around, but do not touch, an affliction 102 of a subject 100. It will be appreciated that the adhesive 25 on the bottom surface 29 of the device 10 may assist in such placement, and keeps the device 10 in position while, for example, a photograph is being taken. The practitioner may refer to the graphical ranking guide 30 and select a rank for the affliction based upon the graphical image 32 and descriptor 42 that most closely match the affliction 102, as optionally suggested by instructions 51. The practitioner may then record his or her assessment of the ranked value for the affliction 102 on, for example, the device itself in a suitable field, or by circling the appropriate rank title indicator or image 32, by entry of the value into a separate form or the like. The practitioner may further record other relevant information where indicated, such as date, practitioner name, affliction location and so forth directly onto the related fields on the top surface 21.

Figure 6:
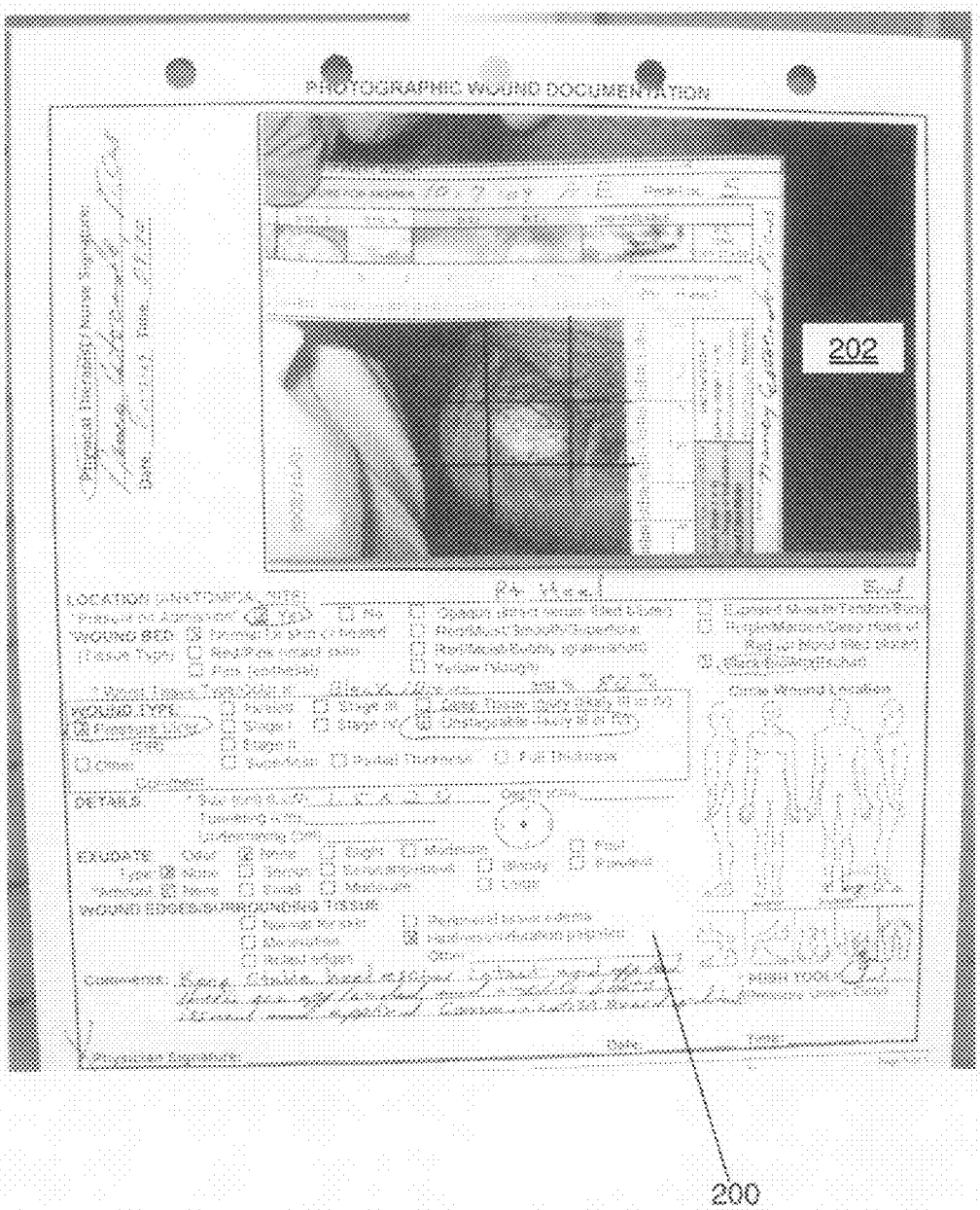
FIG. 6 illustrates a method employing an embodiment device.

FIG. 6 illustrates a particularly preferred method for using the embodiment device 10. In a preferred embodiment method, the practitioner positions the device 10 in contact with the subject to extend around the affliction 102 as described above, and then takes a picture of the affliction 102 with the device 10 visible in the picture around the affliction 102. It will be appreciated that the adhesive 25 keeps the device 10 in contact with the subject, which is convenient for the photography step. Preferably at least the internal origin 16, the first ruler 22 and second ruler 24 are visible in the resultant picture, together with the affliction 102 itself. The picture is then printed in any standard manner and the resultant print 202, which is preferably a color print, is affixed to a form 200, such as with tape, glue, staples or the like, which may then be incorporated into a chart for the subject 100. The print 202 may be used to assist a practitioner in the filling out of fields on the form 200, and provides clear, intuitive evidence of the affliction 102 and the bases for any analysis and diagnosis present in the form 200. Further, as indicated in FIG. 6, a practitioner may mark up the print 202 with lines extending perpendicularly from the arms 12, 14 to the extreme extents of the affliction 102 to approximately assess the surface area of the affliction 102.

Particularly preferred embodiment devices 10 are made from a paper substrate 20, and all graphical and textual information present on the top surface 21 is provided by any suitable printing process, preferably a color printing process to support color graphical images 32. A plurality of such devices 10 may be stacked together, such a stack being mutually held together by the adhesive 25 on the back of each device 10, much like common sticky notes (i.e., Post-it® notes), the top device 10 being peeled off of the stack for use. After single patient use, each device 10 may then be discarded.

It will be appreciated that, with specific reference to the embodiment device 10, any hospital employee that has passed competencies for correctly filling out the device 10 information (date 52, patient initials 53, body part 56, room/location 54, photographer's signature 57, etc.), correct placement on the subject 100 and correct photographing techniques can then provide the picture 202 for the patient's medical record 200. The data captured in the photo 202 may provide valuable information for the appropriate practitioner to assess, fill out additional documentation, begin appropriate interventions and diagnosis within their scope of practice. It will also be appreciated that reliable, objective facts are consequently made available in the medical record 200 from correct use of the device 10. In turn this may facilitate ease for timely choosing correct treatment and prevention interventions, chart coding and for litigation purposes.

It will be further understood that devices 10 may be adapted for different classification systems. The graphical ranking guide 30 and descriptive ranking guide 40 may thus be changed to conform to such other classification systems, thereby illustrating representative rank classifier indicia for each rank in the classification system, and optionally providing corresponding instructions 51. For example, the graphical ranking guide 30 and descriptive ranking guide 40 could be reconfigured to show images and corresponding text illustrative of the various ranks in the burn classification system, the Wagner's Scale for foot ulcers, the Payne Martin Classification for skin tears and so forth.

There is an increasing push to move away from paper to all-electronic filing and docketing. This is particularly true in the medical context. To facilitate this, certain embodiments provide a camera that electronically incorporates a virtual rendering of the above-described assessment tool over the photograph being taken, thereby eliminating the need of the actual physical substrate 20.

Cameras that can take pictures and then determine the scale of items displayed in the resultant photograph are known. For example, U.S. Pat. No. 5,969,822 entitled "Arbitrary-Geometry Laser Surface Scanner," the contents of which are incorporated herein by reference in their entirety, discloses a three-dimensional scanning system that may be handheld and records the position of objects. U.S. published application number 2009/0213213, published Aug. 27, 2009, and entitled "Method of Monitoring a Surface Feature and Apparatus Therefore," the contents of which are incorporated herein by reference in their entirety, discloses a device capable of capturing a surface feature and determining a scale associated with the image. Indeed, handheld devices that permit a user to see the scale of the image taken, and electronically measure the area of a region within the image, are on the market, such as the Silhouette Mobile device from ARANZ Medical Limited of New Zealand.

Figure 7:
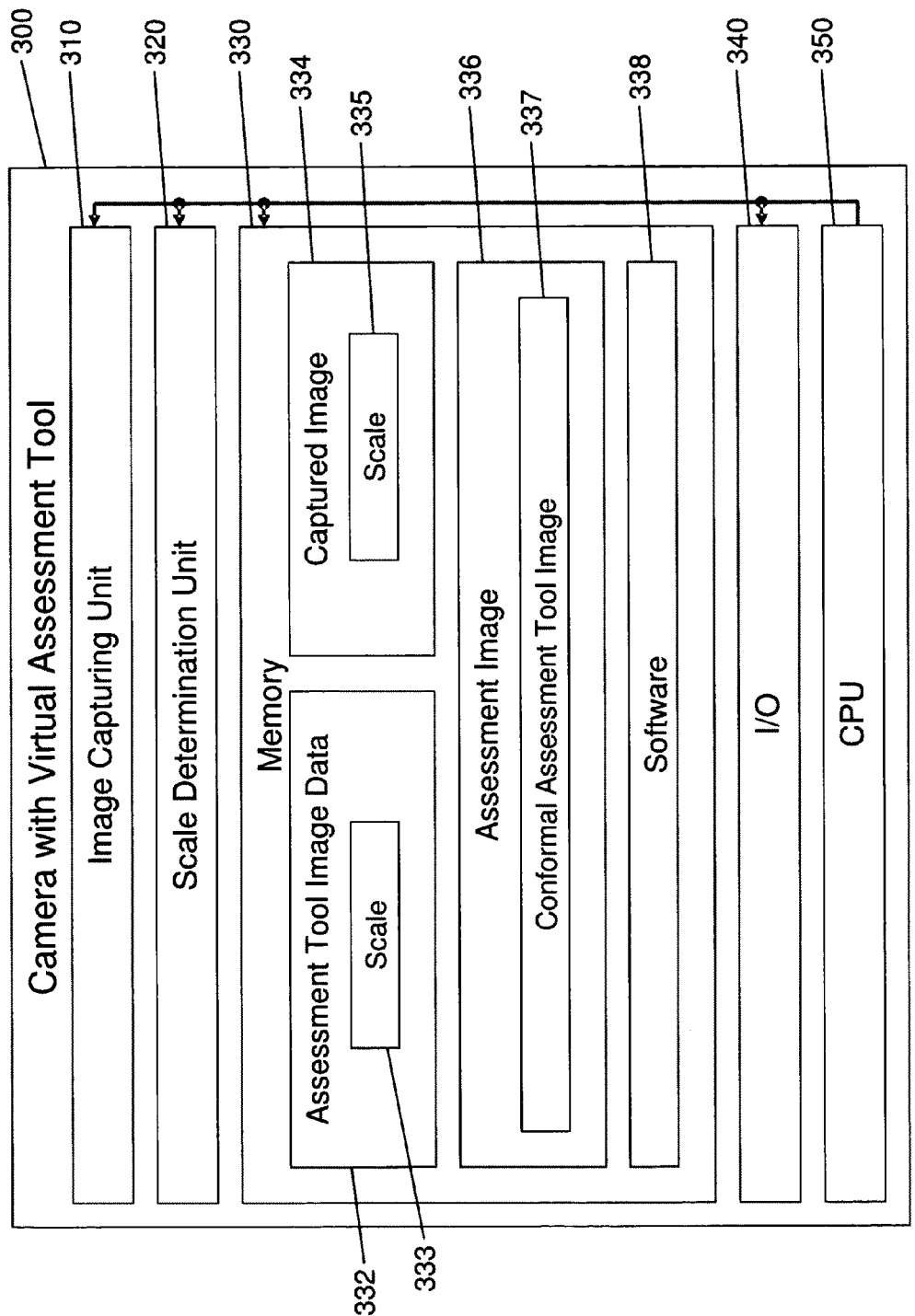
FIG. 7 is a functional diagram of an embodiment digital camera.
Figure 8A:
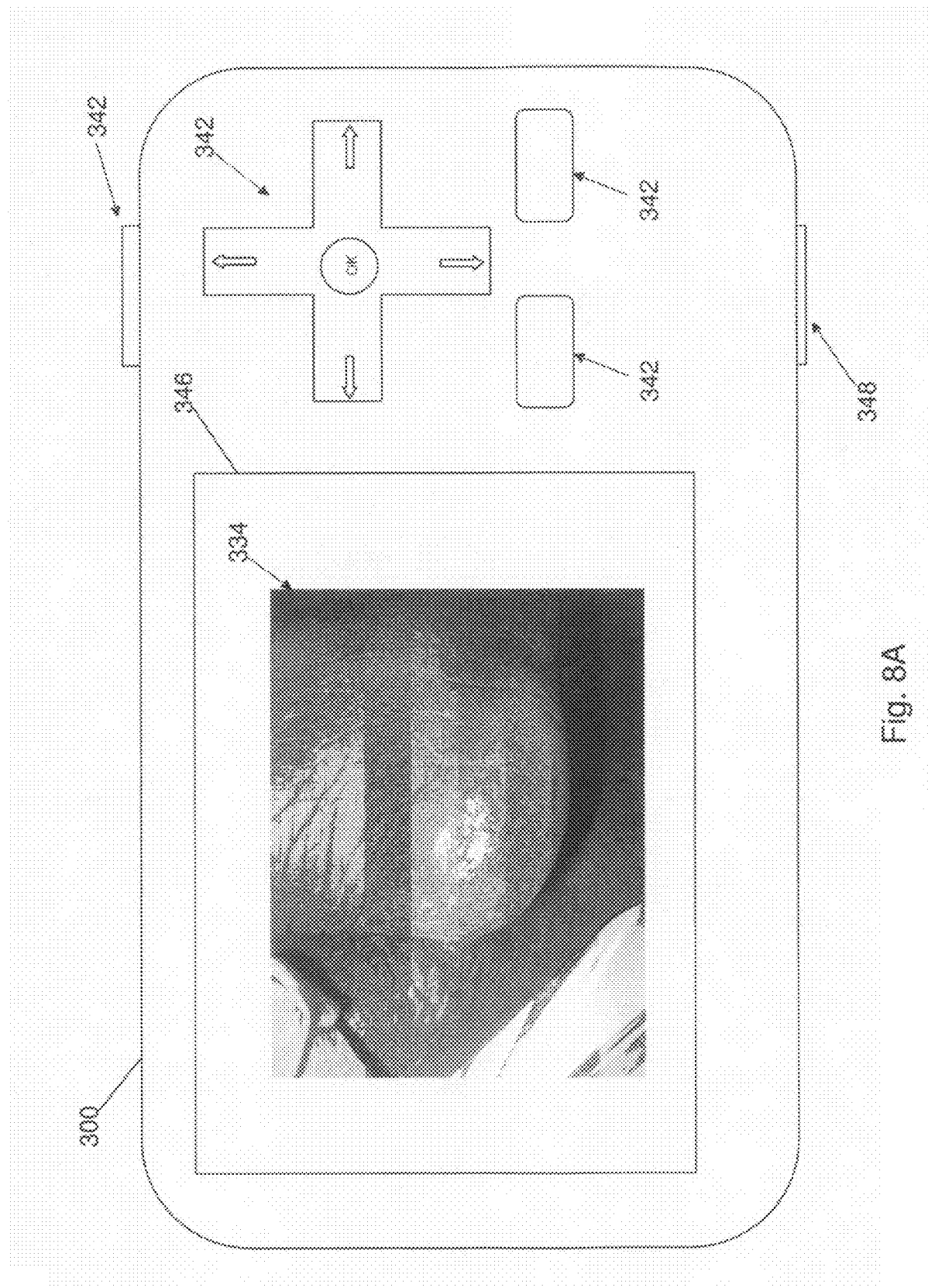

An embodiment device 300 is indicated in FIGS. 7 and 8A-8C. FIG. 7 is a functional diagram of the device 300, while FIGS. 8A-8C show back views of the device 300 with image manipulation being performed by a user according to an embodiment assessment method. The device 300 uses known image capturing and scale determination technology to capture an image and then introduce into that image a virtual representation of the assessment tool discussed above at a scale that is consistent with the determined scale of the image. The device 300 includes an image capturing unit 310, a scale determination unit 320, memory 330, an input/output (I/O) interface 340 and a central processing unit (CPU) 350.

The image capturing unit 310 includes all the components needed to capture an image and store a digital representation of the image 334 in the memory 330; such components may include, for example, a light capturing device, such as a CCD or the like; an optical focusing unit including lenses, a lens driving motor, and the like. Any suitable image capturing unit 310 may be used.

The scale determination unit 320 determines the scale 335 of the image 334 captured by the image capturing system 310. The scale determination unit 320 may include, for example, one or more lasers to create a pre-determined pattern within the view of the image capturing unit 310, optional sensors to determine the tilt of the device 300, and so forth, and may also include software 338 within the memory 330 that is program code executable by the CPU 350 to process collected data and apply an algorithm to obtain the scale 335, which is then stored in the memory 330. Any suitable scale determination system 320 may be used.

The memory 330 may include both volatile and non-volatile memory and is used to store data and software 338 executable by the CPU 350 to provide the functionality of the device 300 as described above and in the following. For example, as indicated the software 338 may include algorithms to obtain the captured image scale 335. The software 338 may also include program code to control the I/O 340 to support a suitable user interface for the device 300. Finally, the software 338 may include code to generate an assessment image 336 that includes a virtual representation of an embodiment assessment tool superimposed onto the image 334 captured by the image capturing unit 310 and at a scale or size that is conformal to the scale 335 of the captured image 336. To this end the memory 330 further includes data 332 representative of an embodiment assessment tool. For example, this may be an actual image 332 of an embodiment assessment tool, such as the device 10, or may be data that is processed by the CPU 350 to generate such an image. This assessment tool image data 332 further includes a scale 333 that indicates the scale of the assessment image data 332.

The I/O 340 may include buttons 342, a display 346 (which may be touch sensitive), a speaker, plugs, data ports 348 (i.e, USB, FireWire, Bluetooth, etc.) and the like to support a user interface and the exchange of data with other devices, as known in the art.

The CPU 350 is in communications with the I/O 340, the memory 330, the scale determination unit 320 and the image capturing unit 310 and executes software 338 to support and control the various units 310-340, to provide a user interface and to provide the overall functionality of the device 300. Any suitable software 338 may be employed to provide the functionality as described herein, and coding such software 338 should be well within the means of one having ordinary skill in the art after having the benefits of this disclosure.

Upon receipt of a signal via the I/O interface 340 to take a picture, the CPU 350 directs the image capturing unit 310 and the scale determination unit 320 to respectively take a photograph and to determine the scale of the resultant image 334. The image 334 and its scale 335 are then stored in the memory 330. The image 334 may be presented on the display 346, as shown in FIG. 8A. Then, such as in response to a user request via the I/O interface 340, the CPU 350 compares the scale 335 of the image 334 to the scale 333 of the virtual assessment tool 332 and performs linear scaling of the assessment tool image data 332 to generate a conformal assessment tool image 337 that is at a scale that equals or substantially equals (i.e., within display tolerances or user viewing tolerances) the scale 335 of the captured image 334. Any suitable image processing algorithm may then be employed by the CPU 350 to superimpose the conformal assessment tool image 337 onto the captured image 334 to thereby generate the assessment image 336. The assessment image 336 may be presented on the display 346, as shown in FIG. 8B, in which the assessment tool image 337 is initially presented in a predetermined location relative to the captured image 334, such as in the upper right hand corner of the captured image 334.

As indicated in FIG. 8C, in preferred embodiments the user interface 342, 346 may permit the user to move the conformal image 337 around the captured image 334, using any suitable image manipulation techniques and user interfaces, to determine the final positioning of the virtual assessment tool image 337 with respect to the captured image 334; once the user is satisfied with the final position, indicated for example via a suitable signal with the I/O 340, the CPU 350 generates the final assessment image 336 with the conformal assessment tool 337 positioned thereon as desired by the user. This assessment image 336 may finally replace the originally captured image 334, or may be stored in the memory 330 together with the captured image 334.

It will be appreciated that in some embodiments the device 300 may permit the user to enter alpha-numeric data via the I/O interface 340, which can then be used to fill in forms or fields in the virtual assessment tool image 337. Hence, data entered by the user into the device 300 may appear within the assessment tool image 337 on the final assessment image 336. This final assessment image 336 may then be downloaded into another device via the data port 348 for printing, insertion into an electronic file or the like.

All publications cited in the specification, both patent publications and non-patent publications, are indicative of the level of skill of those skilled in the art to which this invention pertains. All these publications are herein fully incorporated by reference to the same extent as if each individual publication were specifically and individually indicated as being incorporated by reference.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the following claims.

What is claimed is:

1. A diagnostic tool comprising a first arm and a second arm joined in an L-shaped configuration, a top surface of the first arm comprising a graphical ranking guide comprising a plurality of images that graphically illustrate at least a portion of rank classifier indicia for a classification system comprising a plurality of ranks, each of the images corresponding to at least one of the ranks, a top surface of the second arm comprising a descriptive ranking guide comprising a plurality of rank descriptors containing text describing at least a portion of the rank classifier indicia, each of the rank descriptors corresponding to at least one of the ranks, a bottom surface of the first arm or the second arm comprising an adhesive.

2. A diagnostic tool comprising an antimicrobial or antiseptic agent, and a first arm and a second arm joined in an L-shaped configuration, a top surface of the first arm comprising a graphical ranking guide comprising a plurality of images that graphically illustrate at least a portion of rank classifier indicia for a classification system comprising a plurality of ranks, each of the images corresponding to at least one of the ranks.

3. A diagnostic method comprising:
obtaining an L-shaped diagnostic tool comprising a first arm and a second arm, the first arm or the second arm comprising one or more of a graphical ranking guide and a descriptive ranking guide configured in accordance with a classification system, the first arm and the second arm respectively comprising a first ruler and a second ruler;
disposing the L-shaped diagnostic tool adjacent to an affliction;
taking a picture comprising the affliction and at least a portion of the L-shaped diagnostic tool; and
utilizing the one or more of the graphical ranking guide and the descriptive ranking guide to determine a rank of the affliction within the classification system.

4. The diagnostic method of claim 3 further comprising making a print of the picture and coupling the print to a form.

5. The diagnostic method of claim 3 further comprising utilizing the first ruler and the second ruler to estimate one or more of the area of the affliction, extent of the affliction along the first arm, and extent of the affliction along the second arm.

6. A diagnostic imaging tool comprising:
an image capturing unit;
a scale determination unit;
a central processing unit; and
memory for storing data and program code, the data including assessment tool image data, the program code executable by the central processing unit to perform the following steps:
causing the image capturing unit to capture an image and store the image in the memory as a captured image;
causing the scale determination unit to determine a scale associated with the captured image;
generating a conformal assessment tool image having a scale that is substantially equal to the scale of the captured image; and
generating an assessment image that comprises at least a portion of the assessment tool image and at least a portion of the captured image;
wherein the assessment tool image comprises:
a first arm and a second arm joined in an L-shaped configuration, the first arm comprising a graphical ranking guide comprising a plurality of images that graphically illustrate at least a portion of rank classifier indicia for a classification system comprising a plurality of ranks, each of the images corresponding to at least one of the ranks, and at least one of the arms comprising a ruler conformal to the scale associated with the captured image.

7. The diagnostic imaging tool of claim 6 further comprising an input/output interface, wherein the program code further causes the central processing unit to position the assessment tool image within the assessment image according to instructions received from the input/output interface.

* * * * *